US00PP29177P3

(12) United States Plant Patent
Schoone

(10) Patent No.: US PP29,177 P3
(45) Date of Patent: Apr. 3, 2018

(54) ***PHALAENOPSIS* ORCHID PLANT NAMED 'PURPLE DUST'**

(50) Latin Name: *Phalaenopsis hybrida*
Varietal Denomination: Purple Dust

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 61 days.

(21) Appl. No.: 14/999,287

(22) Filed: Apr. 21, 2016

(65) Prior Publication Data

US 2016/0316606 P1 Oct. 27, 2016

Related U.S. Application Data

(60) Provisional application No. 62/151,686, filed on Apr. 23, 2015.

(51) Int. Cl.
*A01H 5/02* (2018.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen M Redden
(74) *Attorney, Agent, or Firm* — Sunit Talapatra; Foley & Lardner LLP

(57) ABSTRACT

A new and distinct *Phalaenopsis* plant named 'Purple Dust' particularly characterized by flowers which are purple/violet with a white haze in the center; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Purple Dust'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Purple Dust'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Purple Dust' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Purple Dust' originated from a cross made by the inventor in 2002 in Strengweg, Heemskerk, The Netherlands. The female or seed parent is the *Phalaenopsis* cultivar designated 'Carmen', unpatented. The male or pollen parent is the *Phalaenopsis* cultivar designated '(Brother Spring 'Moonlight'×Sogo Smith)', unpatented. The new *Phalaenopsis* 'Purple Dust' was discovered and selected by the inventor as a single flowering plant within the progeny of the stated cross in a controlled environment in 2010 in Strengweg, Heemskerk, The Netherlands.

Asexual reproduction of the new *Phalaenopsis* cultivar by tissue culture (mericloning) was first performed in November, 2010 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Purple Dust', which in combination distinguish this *Phalaenopsis* as a new and distinct cultivar:

1. flowers which are purple/violet with a white haze in the center;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Purple Dust', the flowers of the female parent 'Carmen' are about 8 cm in size and it has a red/purple labellum, the flowers of the male parent '(Brother Spring 'Moonlight'×Sogo Smith)' has light pink colored flowers which are about 10 to 11 cm in size, whereas the flowers of 'Purple Dust' are purple/violet and about 90 mm in size. The labellum of 'Purple Dust' is purple/violet.

Presently, the commercial cultivar to which 'Purple Dust' can be meaningfully compared is 'Flashdance' (U.S. Plant Pat. No. 25,159). The labellum of 'Flashdance' is red/purple, whereas the main color of the labellum of 'Purple Dust' is purple/violet. Also the shape of the labellum differs.

BRIEF DESCRIPTION OF THE PHOTOGRAPHS

The accompanying photographs illustrate the overall appearance of the new *Phalaenopsis* 'Purple Dust' showing the colors as true as is reasonably possible with colored reproductions of this type. Colors in the photographs may differ slightly from the color values cited in the detailed botanical description, which accurately describe the color of 'Purple Dust'.

DETAILED BOTANICAL DESCRIPTION

Figure 1:
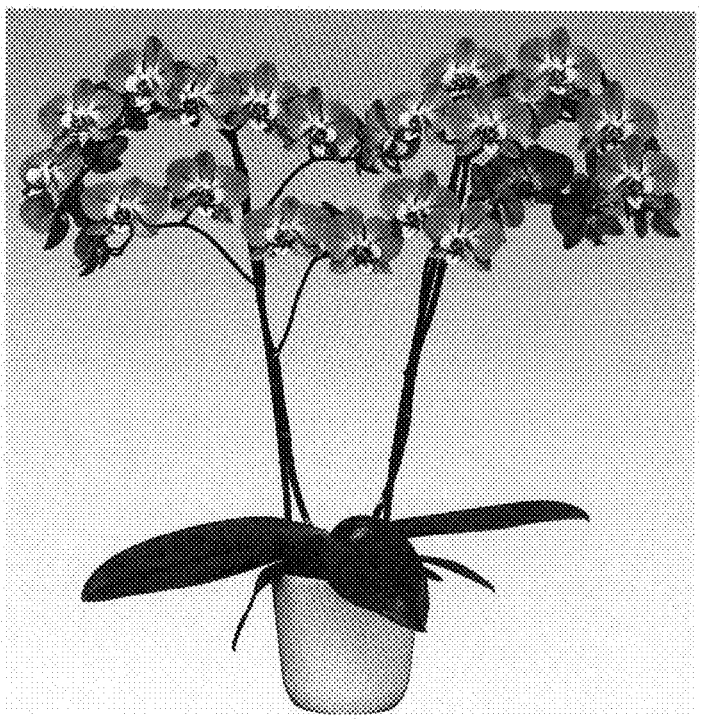
FIG. 1 shows a side view perspective of a typical flowering plant of 'Purple Dust' in a 12 cm pot, at 16 months of age.

The new *Phalaenopsis* cultivar 'Purple Dust' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Purple Dust' as grown in a greenhouse in Strengweg, Heemskerk, The Netherlands, under conditions which closely approximate those generally used in commercial practice. Initially, the ideal temperature to grow plants of 'Purple Dust' is 27° C. during the day and at night. Then, during the flowering phase of 'Purple Dust', the ideal growing temperature is 20-22° C. during the day and 18° C. at night. Light levels for growing 'Purple Dust' are a minimum of 5,000 lux and a maximum of 10,000 lux. A balanced fertilizer with level of 200 ppm N, 87 ppm P, 168 ppm K is applied. Duration of growth of 'Purple Dust' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Purple Dust' plants described is 12 months after potting.

Classification:

*Botanical.—Phalaenopsis hybrida.*

Parentage:

*Female or seed parent.—Phalaenopsis* cultivar designated 'Carmen', unpatented.

*Male or pollen parent.—Phalaenopsis* cultivar designated '(Brother Spring 'Moonlight'×Sogo Smith)', unpatented.

Propagation:

*Type.*—Tissue culture.

*Rooting habit and description.*—Fleshy; approximately 3 mm-5 mm wide and greyed/green in color (RHS 190A and RHS 191A); freely branching. It takes 12 weeks for plants growing in tissue culture to initiate roots Plant:

*Size at maturity.*—Height (from bottom of pot to highest flower): about 60 cm. Spread: about 50 cm.

*Growth habit.*—Standard; green leaves (RHS 137B and RHS 137C) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 6-8 leaves are produced before flowering.

*Arrangement and attachment.*—Half up/horizontal and on two sides.

*Overall shape of leaf.*—Oval; the tip is blunt and asymmetric.

*Texture (upper & underside).*—Smooth and leathery.

*Pubescence.*—None.

*Mature leaf length.*—About 20 cm.

*Mature leaf width.*—About 7 cm.

*Mature leaf thickness.*—About 2 mm.

*Mature leaf color.*—Upper side: green (RHS 137B and RHS 137C). Under side: green (RHS 137B) with greyed/orange on the edges (RHS 172A).

*Leaf base.*—Acute.

*Margin.*—Entire.

*Venation.*—Pattern: parallel. Color of midvein: upper side: green (RHS 137A). Under side: green (RHS 138A) and greyed/orange (RHS 172A).

Inflorescence description:

Appearance: Upright to slightly pendant, racemose inflorescence with bilaterally symmetrical flowers that open in succession beginning with the lowermost flower.

Raceme:

*Quantity per plant.*—About 1 to 2.

*Number of flowers per raceme.*—About 7-19.

*Length.*—About 15-35 cm.

*Diameter.*—About 4 mm.

Peduncle:

*Length.*—About 25-40 cm.

*Diameter.*—About 4 mm.

*Strength.*—Strong.

*Aspect.*—Upright.

*Texture.*—Glabrous and smooth.

*Color.*—Brown (RHS N200A) with yellow/green (RHS 146A).

Buds:

*Height (from base to tip).*—About 25 mm.

*Diameter (at midpoint).*—About 18 mm.

*Shape.*—Oval.

*Color*.—Purple (RHS N80B) with yellow/green (RHS 146D).

*Orientation*.—Same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
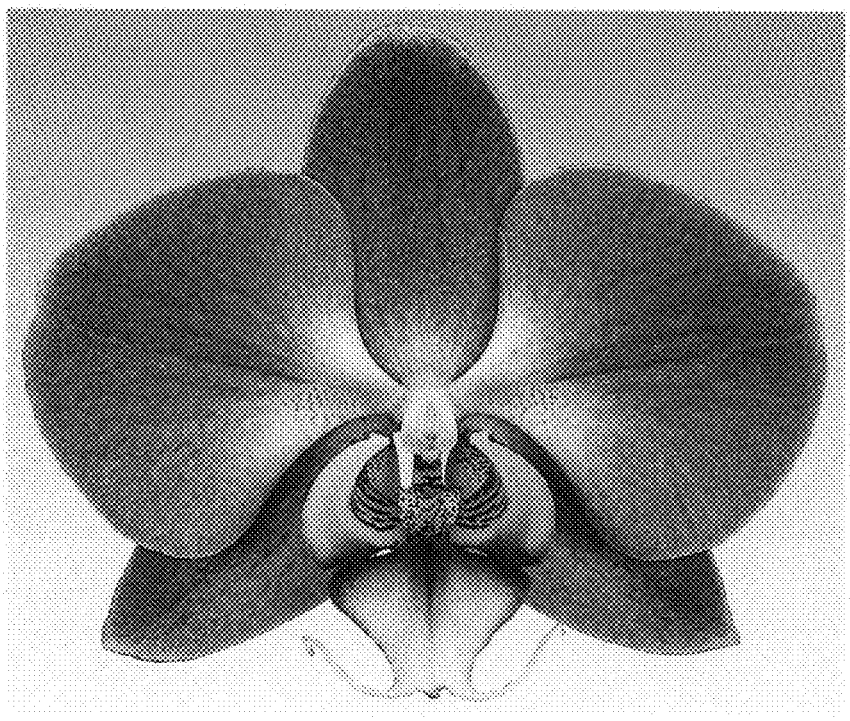
FIG. 2 shows a close-up view of the typical flower of 'Purple Dust'.
Figure 3:
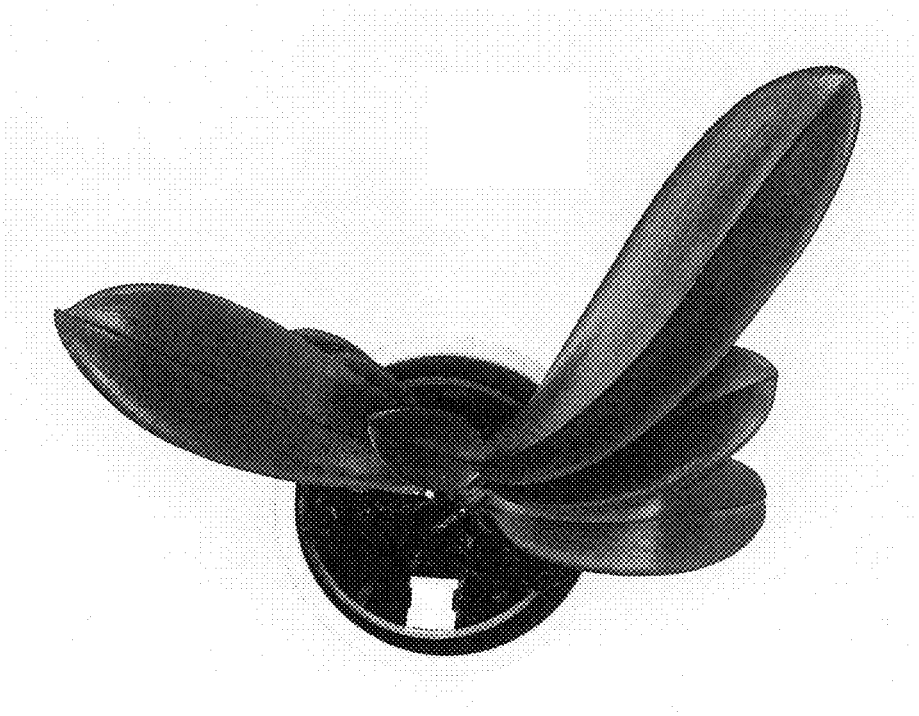
FIG. 3 shows a close-up view of the typical leaves of 'Purple Dust'.

*Shape*.—Typical shape of *Phalaenopsis*; see FIG. 2.

*Size* (*of single bloom*).—Height: about 70 mm. Width: about 90 mm.

*Quantity and arrangement*.—Three petals and three sepals that are trimerous, overlapping and arranged in 2 whorls. Petals are more pronounced than sepals.

Petals:

*Arrangement*.—Inner whorl comprises 3 petals: 2 lateral petals and a labellum.

2 *Lateral petals*.—Overall shape: broadly ovate and weakly cupped. Apex: oval. Margin: entire and weakly undulate. Base: broadly ovate. Length: about 45 mm. Width: about 40 mm. Texture: Upper surface: smooth and satiny. Under surface: smooth and satiny. Color (when fully opened): upper side: main color is purple/violet (RHS N80B with some RHS N80A). At the base some white (RHS NN155C) and also a thin white line round the edges (RHS NN155C). Under side: main color is purple/violet (RHS N80B with some RHS N80A) with a white haze (RHS NN155C). At the base some purple/violet (RHS N80A) and also some white at the edges (RHS NN155A). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex of the midlobe and lateral lobes: oval. Length midlobe: about 20 mm. Width midlobe (not flattened): about 22 mm. Length lateral lobe: about 20 mm. Width lateral lobe (not flattened): about 15 mm. Depth of tube created by lateral lobes of labellum: about 15 mm. Texture: Upper & under surface: smooth and satiny. Color (when fully opened): Mid lobe, upper side: main color is purple/violet (RHS N80D) with some purple/violet (RHS N80B) in the center. Upper edges and midvein red/purple (RHS 59B). At the corners and on the midvein also some greyed/orange (RHS 167A). Under side: purple (RHS N78C with some RHS N78B). At the upper edges some greyed/orange (RHS 167BA). Lateral lobes, upper side: white (RHS NN155C) with some purple/violet (RHS N80C). At the lower edges greyed/orange (RHS 172B) which runs into yellow (RHS 10A). From the base some red/purple stripes (RHS 59B). Under side: the lower part is purple/violet (RHS N80B) with at the lower edge a yellow haze (RHS 13A). The upper part is white (RHS NN155C). Cirrhi: about 15 mm. Color: purple/violet (RHS N80D) which runs into white (RHS NN155C). Pestle (Callosities): Length: about 5 mm. Width (not flattened): about 7 mm. Color: main color is yellow (RHS 13A) with some white hazes (RHS NN155C) and with red/purple spots and stripes (RHS 59A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 46 mm.

*Width*.—About 26 mm.

*Apex*.—Oval and little pointy.

*Texture*.—Upper and under surface: smooth and satiny.

*Color* (*when fully opened*).—Upper side, dorsal: purple/violet (a combination between N80A and N80B) with some small purple spots (RHS 76C) and some purple at the base (RHS 76A). Lateral: purple/violet (a combination between N80A and N80B) with some small purple spots (RHS 76C). At the base some white (RHS NN155) with yellow/green (RHS 150D) and red/purple spots (RHS 59A). Under side, dorsal: purple/violet (a combination between N80A and N80B). Lateral: purple/violet (a combination between N80A and N80B) with at the base some yellow/green (RHS 150D).

Pedicel:

*Length*.—About 52 mm.

*Diameter*.—About 3 mm.

*Texture*.—Glabrous and smooth.

*Color*.—Starting at the flower white (RHS NN155C) which runs into yellow/green (RHS 145C) and then brown (RHS 200B).

Reproductive organs:

Arrangement: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed to date.

Column:

*Length*.—About 11 mm.

*Diameter*.—About 5 mm.

*Color*.—White (RHS NN155C) with some purple/violet (RHS N80B).

Pollinia:

*Quantity*.—Two.

*Diameter*.—About 2 mm.

*Color*.—Yellow/orange (RHS 23A).

Ovary:

*Length*.—About 5 mm.

*Diameter*.—About 5 mm.

*Color*.—White (RHS NN155C).

Disease/pest resistance/ susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Purple Dust', as illustrated and described herein.

* * * * *